US008948875B2

(12) United States Patent
Paulus et al.

(10) Patent No.: US 8,948,875 B2
(45) Date of Patent: Feb. 3, 2015

(54) DEVICE FOR NON-INVASIVE, ELECTRICAL DEEP-BRAIN STIMULATION

(75) Inventors: Walter Paulus, Göttingen (DE); Udo Warschewske, Berlin (DE)

(73) Assignee: EBS Technologies GmbH, Kleinmachnow (DE)

( * ) Notice: Subject to any disclaimer, the term of this patent is extended or adjusted under 35 U.S.C. 154(b) by 0 days.

(21) Appl. No.: 13/995,855

(22) PCT Filed: Dec. 21, 2011

(86) PCT No.: PCT/EP2011/073619
§ 371 (c)(1),
(2), (4) Date: Aug. 28, 2013

(87) PCT Pub. No.: WO2012/089588
PCT Pub. Date: Jul. 5, 2012

(65) Prior Publication Data
US 2013/0345774 A1     Dec. 26, 2013

(30) Foreign Application Priority Data

Dec. 28, 2010   (DE) .......................... 10 2010 056 433
Dec. 5, 2011    (DE) .......................... 10 2011 120 213

(51) Int. Cl.
*A61N 1/00*     (2006.01)
*A61N 1/36*     (2006.01)
*A61N 1/32*     (2006.01)

(52) U.S. Cl.
CPC ............ *A61N 1/36025* (2013.01); *A61N 1/323* (2013.01); *A61N 1/36014* (2013.01)
USPC .......................................................... 607/45

(58) Field of Classification Search
CPC .................................................... A61N 1/0534
USPC ............................................. 607/2, 9, 14, 45
See application file for complete search history.

(56) References Cited

U.S. PATENT DOCUMENTS
4,856,526 A     8/1989 Liss et al. ....................... 607/46
2003/0236558 A1* 12/2003 Whitehurst et al. ............ 607/45
(Continued)

FOREIGN PATENT DOCUMENTS
DE      102008043973      6/2010     ............... A61N 1/20

OTHER PUBLICATIONS
Notification Concerning Transmittal of International Preliminary Report on Patentability (Chapter I of the Patent Cooperation Treaty), in English, dated Jul. 11, 2013, International Preliminary Report on Patentability (Chapter I of the Patent Cooperation Treaty), in English, dated Jul. 2, 2013, Written Opinion of the International Searching Authority, in English (Jul. 2, 2013—mailed with Notification Concerning Transmittal of the International Preliminary Report on Patentability), Notification Concerning Transmittal of the International Search Report and Written Opinion of the International Searching Authority, in English, dated Feb. 21, 2012, and International Search Report, in English, dated Feb. 21, 2012, each of which was issued by the International Bureau of WIPO for corresponding PCT Application No. PCT/EP2011/073619, filed on Dec. 21, 2011.
(Continued)

*Primary Examiner* — Christopher D Koharski
*Assistant Examiner* — Nadia Mahmood
(74) *Attorney, Agent, or Firm* — Gerald T. Bodner

(57) ABSTRACT

The invention relates to a device and a method for transcranial, non-invasive, electrical deep-brain stimulation, of the kind used in particular in the treatment of neurological and psychiatric disorders and of disturbances of the motor/cognitive functions in the human brain, wherein the device has at least one signal generator for generating an electrical alternating-current signal, an electrode arrangement, which can be placed on the head of a person to be treated and can be connected electrically to the signal generator so as to apply an alternating-current signal, wherein the electrode arrangement can be used to apply at least two alternating-current signals, of which the trajectories cross the region of the brain to be treated, such that their alternating currents are superposed, as a result of which the region of the brain to be treated is stimulated by electrical alternating currents in a targeted manner, whereas adjacent regions of the brain are stimulated only slightly or not at all.

20 Claims, 6 Drawing Sheets

(56) References Cited

U.S. PATENT DOCUMENTS

| | | | |
|---|---|---|---|
| 2006/0173510 A1 | 8/2006 | Besio et al. | 607/45 |
| 2009/0287108 A1 | 11/2009 | Levy | 600/544 |
| 2011/0288610 A1 | 11/2011 | Brocke | 607/45 |
| 2012/0245653 A1* | 9/2012 | Bikson et al. | 607/45 |

OTHER PUBLICATIONS

Antal, et al., "*Comparatively weak after-effects of transcranial alternating current stimulation (tACS) on cortical excitability in humans,*" Brain Stimulation, vol. 1, No. 2, Apr. 2008, pp. 97-105.

Paulus, et al., "*On the difficulties of separating retinal from cortical origins of phosphenes when using transcranial alternating current stimulation (tACS),*" Clinical Neurophysiology, vol. 121, No. 7, Jul. 2010, pp. 987-991.

Zaghi, et al., "*Inhibition of motor cortex excitability with 15Hz transcranial alternating current stimulation (tACS),*" Neuroscience Letters, vol. 479, No. 3, Aug. 2010, pp. 211-214.

Kanai, et al., "*Transcranial alternating current stimulation (tACS) modulates cortical excitability as assessed by TMS-induced phosphene thresholds,*" Clinical Neurophysiology, vol. 121, No. 9, Sep. 2010, pp. 1551-1554.

Schutter, et al., "*Retinal origin of phosphenes to transcranial alternating current stimulation,*" Clinical Neurophysiology, vol. 121, No. 7, Jul. 2010, pp. 1080-1084.

Park, et al., "*A Novel Array-Type Transcranial Direct Current Stimulation (tDCS), System for Accurate Focusing on Targeted Brain Areas,*" IEEE Transactions on Magnetics, vol. 47, No. 5, May 2011, pp. 882-885.

\* cited by examiner

DEVICE FOR NON-INVASIVE, ELECTRICAL DEEP-BRAIN STIMULATION

The present invention relates to an apparatus and a method for the transcranial, non-invasive, electrical deep brain stimulation, of the kind used in particular for the treatment of neurological and psychiatric disorders and disturbances of the motor/cognitive functions in the human brain.

The electrical deep brain stimulation (DBS) is, in general, a neurosurgical precision process in which brain structures, in particular abnormally overactive core regions in the brain are inhibited by supplying a low amplitude current, so that the obstructive symptoms can be effectively alleviated. The exact functional principle and principle of operation of the deep brain stimulation are still not clear until now and, therefore, object of intensive research.

Established fields of application are, inter alia, the Parkinson's disease, the essential tremor, or dystonia. In clinical tests applications are found in the fields of epilepsy, depression, obsessive-compulsive disorder, cluster headache, and Tourette syndrome.

According to the prior art a difference is presently made substantially between two basic methods for the electrical deep brain stimulation, viz. the invasive deep brain stimulation and the non-invasive deep brain stimulation.

According to the prior art the invasive deep brain stimulation is a neurosurgical intervention in the brain, by means of which malfunctions caused by a disease are to be corrected. For the chronic brain stimulation the patient is usually implanted one or two thin electrodes which are connected, by subcutaneously laid cables, to a pulse generator in the breast region or upper abdomen. This pulse generator permanently supplies electric pulses to the target region in the brain, so that this region can either be deactivated or stimulated, depending on the current frequency. As the electric pulses in the invasive deep brain stimulation are supplied permanently this method is also called chronic deep brain stimulation. The associated medical devices are known by the common designation "brain pacemaker".

Until now approximately 75,000 patients worldwide were operatively provided with a brain pacemaker. Prospective, controlled and randomized studies in recent years demonstrate the constant effectiveness of the therapeutic method in the individual course of a disease. Not only symptoms of the disease like trembling (tremor), rigidity (rigor) and lack of motion (bradykinesia) get better, but provably also the quality of life in holistic terms.

In the operative treatment by means of deep brain stimulation, which is also referred to as "stereotactic" operation, the electrodes are usually introduced into the brain through a small borehole in the skull of the person to be treated, and are accurately placed in the region of the brain area to be stimulated. Thus, it is possible to manipulate the brain activity by electrical stimulation, selectively, and permanently or chronically, at previously precisely fixed positions in the brain.

Apart from the high costs for such invasive operations in the human brain, above all the health risks, such as the occurrence of brain bleeding or brain infections, have to be calculated in advance. It should be considered that there is not only a direct health risk by the surgical intervention itself, but there will also be latent health risks during the whole duration of the treatment due to the implants. The advantage of the invasive stimulation methods is the precision with which the corresponding brain areas can be subjected to a targeted deep brain stimulation treatment, and the possibility of a chronic and permanent treatment.

The non-invasive methods in the field of the electrical neurostimulation of brain areas relate to the so-called transcranial methods for the non-invasive deep brain treatment, in particular the transcranial direct current stimulation (tDCS) and the transcranial alternating current stimulation (tACS), where a therapeutic stimulation is carried out without an interventional operation in the brain. Instead, the treatment is carried out "transcranially", that is, from outside of the skull, "through the skull". Both, the transcranial direct current stimulation (tDCS) and the transcranial alternating current stimulation (tACS) employ two electrodes, which are placed on the scalp of the patient and are supplied with a direct current or alternating current for a limited length of time of up to 15 minutes in order to stimulate the neuronal circuits in the brain.

A method for the transcranial alternating current stimulation for the reduction of headaches is known from U.S. Pat. No. 4,856,526, according to which a high-frequency alternating voltage is applied by two electrodes placed on the patient's head. The frequency range of the alternating voltage is in the range between 12 and 20 kHz. For the treatment, a first electrode is placed on one side of the head, and another electrode is placed on the opposite side of the head.

DE 102008043973 A1 discloses a device for the transcranial direct current stimulation (tDCS) which is used for the treatment and stimulation of neuronal brain structures. In this method a weak continuous direct current is applied to the scalp by means of a large-surface electrode arrangement, which is positioned in a cap, for instance, in a grid-like manner. To adjust an optimal electrode surface, which allows a focusing of the induced overall charge in the central nervous system, individual electrode pairs of this quantity of plate electrodes, which are arranged in a grid-like manner, can be excited for stimulation purposes. The determination of this optimal electrode surface is carried out by taking into account the transition resistance between the electrode surface and the scalp. By selectively triggering individual electrode areas of the grid-like array the whole contiguous electrode surface is variably adjustable to apply a direct current. That is, the electrode surface used may be chosen to be larger or smaller so as to stimulate a brain area positioned between the electrode arrangement to a greater or smaller extent (focusing of the induced overall charge).

As, in contrast to the invasive deep brain stimulation, the non-invasive, transcranial, electrical deep brain stimulation requires the application of a higher stimulation current due a higher resistance, i.e. transition resistance between electrodes and head or scalp of the patient, so as to supply the overall charge necessary for the successful treatment in the brain area, the duration of the treatment with a direct current stimulation is limited to approximately 15 minutes for safety reasons.

In the transcranial direct current stimulation (tDCS) long-term effects were found with regard to the stimulation treatment. After switching off the active stimulation current, a direct current stimulation of approximately 10 minutes effects an increased excitability in the treated brain area of up to one hour, and a direct current stimulation of approximately 15 minutes effects an increased excitability in the treated brain area of up to two hours.

The study of Park et al. (NOVEL ARRAY-TYPE TRANSCRANIAL DIRECT CURRENT STIMULATION (tDCS) SYSTEM) deals with methods for increasing the density/intensity of the stimulating direct current in the brain area to be treated. In a first solution two electrodes are placed on the head such that the trajectory of the stimulating direct current runs precisely through the brain area to be treated. In a second solution two electrode arrays are used, which form several electrode pairs in a spatial arrangement, with oppositely arranged electrodes each defining one electrode pair. The individual electrode pairs, again, may be triggered by different direct current signals. To obtain the optimum stimulation current density in the brain area to be treated the resistance distributions are determined by means of a skull model, on the basis of which the current intensities to be injected into the individual electrode pairs to obtain an improved stimulation current density are determined. The determination of the optimal injected current distributions is based on the superposition principle.

A significant disadvantage of the direct current stimulation (tDCS) is that by the use of plate electrodes the maximum effective area of the direct current is not at the positions of the electrodes, so that a cortically locally focused therapy is possible only to a limited extent.

Another disadvantage is that the trajectories formed when a current is applied run substantially in parallel, or at least side by side. Although the current densities in the brain area are thus increased, the treatment still affects brain areas that are directly adjacent to the target area intended for the treatment. Therefore, a targeted stimulation treatment is possible only to a limited extent.

Finally, the continuous maximum treatment duration involved by the known methods and apparatus for the non-invasive, electrical deep brain stimulation is still not satisfactory. Hence, there is a need for a method and an apparatus for the transcranial electrical deep brain stimulation that allow longer treatment phases.

It is, therefore, the object of the present invention to provide an apparatus and a method for the non-invasive, electrical deep brain stimulation by means of which a targeted and effective treatment of brain areas is possible in a simple and cost-effective manner.

This object is achieved by the features recited in the independent claims 1 and 15. Advantageous embodiments are described in the dependent claims.

According to the invention this object is achieved by an apparatus for the transcranial alternating current stimulation (tASC) of deep brain areas, comprising at least one signal generator for generating an electrical alternating current signal, an electrode arrangement which can be placed on the head of a person to be treated and can be connected electrically to the signal generator so as to apply an alternating current signal, wherein at least two alternating current signals can be applied by means of the electrode arrangement, whose trajectories cross the brain area or brain region to be treated. Trajectories in this context are space curves along which the alternating currents travel through the brain of a person to be treated.

To this end, the inventive finding is used that the trajectories are nearly straight-lined trajectories if alternating currents with a frequency in the kHz range are used. As opposed to this, alternating currents having a frequency of less than 200 Hz flow along the nerve fibers, which renders a precise, target-aimed treatment difficult.

The central idea of the invention consists in carrying out a therapeutic stimulation without an invasive interventional intervention in the brain. To this end, the functional area of the brain in question is selectively excited with electrical alternating currents. At the same time, adjacent areas are not affected, or only to a small or below-threshold extent. This is obtained by a special spatial arrangement of the electrodes, between which the electrical stimulation is applied by means of an alternating current in such a manner that the stimulation trajectories cross the area to be stimulated deep down, so that a compression of the stimulation current is obtained, and thus a focusing of the energy supply in the area to be treated. It was found that, inter alia, the relative stimulation difference between the current density injected in the target region and the surrounding brain areas is significant for the effectiveness of a deep brain stimulation. The greater the relative difference of the current densities in the target area and the areas adjacent to the target area, the greater the stimulation effect.

As opposed to the application of a direct current, the application of an alternating current further brings about an enhanced aftereffect of the electrical stimulation. Although it was found in both the transcranial alternating current stimulation (tACS) and the transcranial direct current stimulation (tDCS) that in a corresponding short-term treatment up to 10 minutes the stimulation effect is maintained after the active stimulation current is switched off, which means that a certain long-term effect is achieved, it could be found on the whole that the transcranial alternating current stimulation (tACS) brings greater long-term effects as opposed to the transcranial direct current stimulation (tDCS), i.e. a maintenance of the stimulation effect, which is due to the rising and falling stimulation effect, rising and falling in terms of time, caused by the alternating current.

Furthermore, the electrode arrangement can be placed on the head and/or the applied alternating current can be adjusted with respect to the amplitude and/or the frequency in such a manner that the trajectories of at least two applied alternating current signals cross each other in the target region. In particular, starting out from two different planes, the trajectories may cross each other in the target region, especially in a defined point which is preferably located in the spatial center of the target region, so that the superposition effect in the target region is further intensified, while the surrounding brain areas are even less affected. Thus, the stimulation difference between the target region and adjacent brain regions can be increased and, accordingly, the stimulation effect improved.

Preferably, an applied current signal is a high-frequency alternating current signal with a frequency of between 1 kHz and 50 kHz. Surprisingly, alternating current signals with such a high frequency result in an increased stimulation effect in the target region, which is due to the increased sensitivity of neuronal networks by the modulation of the electric field in the target region.

The applied alternating current signal is preferably a pulsed alternating current signal. However, it is also possible to apply other alternating current signal shapes, e.g. a sine wave signal shape, a triangular signal shape, a sawtooth signal shape, but also a noise signal. As stimuli in the human conduction system are typically transmitted in the form of electric pulses, a pulsed alternating current signal advantageously allows to achieve an approximation to the curve shape inherent in the human body, and thus an improved excitation effect and stimulation effect, respectively. The electrical stimulation parameters such as frequency, amplitude, curve shape and pulse sequence of the alternating current signal, and the duration of the stimulation, the sequence of therapeutic sessions in terms of time, and the size and location of the target area can be varied according to the therapeutic approach.

According to an advantageous embodiment the electrode arrangement comprises at least two electrode pairs, which can be spatially positioned in such a manner that the trajectories of at least two applied current signals cross the target region, or cross each other in the target region where they concentrate and are intensified.

According to an advantageous further development of the invention a current application control device is provided to control the current signals applied to the at least one electrode pair, which can be operated in such a manner that the at least two current signals are applied sequentially, in particular alternately. Accordingly, current signals are applied successively, which cross the target region along different trajectories, resulting in a permanent stimulation effect in the target region, while stimulation-free phases are obtained for the brain areas adjacent to the target region, so that the excitation effect can be further reduced in these areas.

Advantageously, the application of a high-frequency alternating current and the sequential control allow to achieve an increased stimulation in the target area, along with a reduced excitation effect in the surrounding brain area. For instance, a total of two electrode pairs may be provided in different spatial arrangements, i.e. a first and a second position on the head of the person to be treated, and an alternating stimulation current is alternately supplied to the electrode pair at the first and the second position. Preferably, the alternating current pulses are each applied for a very short period only.

According to a preferred embodiment of the solution the electrode arrangement comprises an electrode array pair, wherein each electrode array comprises a plurality of electrodes arranged in a grid-like or matrix-like manner, wherein preferably one electrode array acts as a target electrode and one electrode array acts as a reference electrode, and wherein the number of the target electrodes corresponds to the number of the reference electrodes. However, it is also possible that an electrode pair, consisting of an electrode array which defines for instance the target side, and an individual electrode which correspondingly defines the reference side, is provided.

In case of using, for instance, prefabricated electrode arrays, same are spatially correlated with the target region. Then, those electrode pairs are determined and used whose trajectories cross the target region. According to an advantageous further development of the invention the current application control device is capable, to this end, of choosing and controlling precisely those electrode pairs from the plurality of electrodes whose current signal trajectories cross the target region, in particular whose current signal trajectories cross each other in the target region. The current application control device is capable of sequentially controlling and activating these electrode pairs depending on the course of the therapy in terms of time and a corresponding preselection of electrode pairs.

For instance, the electrode pairs may be directly connected to several independent stimulation signal generators and triggered independently. In a preferred embodiment the current application control device comprises a matrix switch, and a controller device controlling the matrix switch. By means of the matrix switch a freely selectable electrode pair can be assigned to a signal generator or function generator, wherein the switching of the electrodes by means of the matrix switch through the controller is coordinated with the signals of one or more signal generators or function generators.

Fixing one or more electrode pairs or the electrode arrays in a spatial arrangement on the head of the person to be treated is accomplished by a fixing means. The fixing means may be a belt or a cap, wherein the electrode arrays or the individual electrodes are integrated in the respective fixing means. In the simplest case the electrodes are provided in the form of plate electrodes, in particular adhesive electrodes, which have an adhesive portion in the area of the contact surface of the electrodes.

Preferably, the electrodes of the electrode pairs are planar and preferably have a surface of some $mm^2$ to $cm^2$.

The cap may be made of a textile spacer fabrics with integrated electrodes.

According to another preferred embodiment a possibility of the volumetric stimulation concept consists in displacing an electrode pair fast and selectively, e.g. by a navigable mechatronic device, to adopt positions in a specific sequence. Thus, the energy supply is focused to the area to be treated, while surrounding areas of the brain are affected only to a limited extent. To this end, the current application control device comprises a positioning apparatus on which an electrode pair is provided, wherein the positioning apparatus holds the electrode pair on the head of the person to be treated in a first electrode pair position and in a second electrode pair position, wherein the first and the second spatial electrode pair positions are offset relative to each other in such a manner that the trajectories of the current signals applied in the first and in the second electrode pair positions cross the target region, or the trajectories of these current signals cross each other in the target region. The current application control device further comprises a controller device which predefines the operation of the positioning apparatus and the operation of the function generator so as to coordinate the positioning of the electrode pair and the current application in the different electrode pair positions.

One advantageous further development of the invention consists in the determination of the location and dimensions of the target region on a planning station. The basis for the target planing are, for instance, volumetric anatomical image data, such as CT or MRT. In addition, the areas can also be delimited by means of functional brain atlases (e.g. atlas by Schaltenbrand-Wahren). Other planning possibilities are based on the use of spatial functional data, such as fMRT, 3D $EEG^2$, or the impedance tomography. Also, it is possible to correlate several data sets with each other (e.g. by the multimodal image data fusion).

The spatial correlation of the electrode pairs with the patient's brain or target region, respectively, can be accomplished, for instance, by means of an image-supported navigation. In this case, the spatial data in respect of the target region are matched with the position system of the navigation system and extended by the positions of the electrode pairs. If preconfigured electrode arrays are used, they may be fixed to the head, for instance, by means of molding material or suited bite plates, so that in the case of reuse the fit ensures an accurate correlation with the target region, and a new correlation of the electrodes with the target region is not necessary.

The spatial correlation of electrode position and target area may also be accomplished without the use of an additional position measurement system. To this end, the electrodes are directly localized in a data set (e.g. by image data analysis, if suited CT or MRT markers are used on the electrodes or electrode bases, by referencing to electrodes of the 3D EEG derivation, or impedance tomography). In a second step, stimulation sequences are specified using suited electrode pairs, and suited stimulation parameters are chosen for the therapeutic target.

In addition, a feedback device is provided for recording the bio-feedback of the patient and allow an evaluation of the therapeutic success or, if necessary, recognize dangers to the patient (e.g. epileptic fit). The feedback data may be used in a feedback control system which is monitored by the controller, so as to optimize the stimulation parameters.

The apparatus as described and claimed in claims 1 to 15 is employed in methods for the treatment of functional disorders of the brain, in particular for the therapeutic treatment of the Parkinson's disease, in particular trembling (tremor), rigidity (rigor), lack of motion (bradykinesia), apoplectic fit, paralyzations, depression, schizophrenia, obsessive-compulsive disorders, anxiety disorders and panic disorders, dementia, focal neuropsychological deficits, multiple sclerosis, restless legs syndrome, pains, headache, migraine, dystonia, epilepsy and the Tourette syndrome.

Furthermore, a method is proposed for the transcranial, non-invasive alternating current stimulation (tACS) of deep brain areas, comprising the steps of:

placing at least two electrode pairs at positions on the head of a person to be treated at which the trajectories of the applied alternating current signals cross the brain area or target region to be treated, or the trajectories of the alternating current signals cross each other in the target region; or placing an electrode array pair in correlation with the target region to be treated on the head of a person to be treated and determining the pairs of electrodes whose trajectories cross the target region or whose trajectories cross each other in the target region; connecting the electrode pairs to the alternating current source; and applying an alternating current signal to the electrodes for stimulating the target region.

Preferably, an alternating current signal is applied to the electrode pairs simultaneously, or sequentially or successively, respectively, in particular alternately. Preferably, the alternating current signal is adjusted to a frequency of between 1 kHz and 50 kHz, and/or the alternating current signal is applied as a pulsed alternating current signal, and/or the electrical stimulation parameters such as frequency, amplitude, curve shape and pulse sequence are varied.

Preferably, the brain areas to be stimulated are determined before the stimulation treatment, in particular the location and dimensions thereof, in particular by means of volumetric anatomical image data, e.g CT or MRT.

Furthermore, a method is proposed for the transcranial, non-invasive alternating current stimulation (tACS) of deep brain areas, comprising the steps of:

providing an electrode pair and connecting the electrode pair to the alternating current source; successively placing the electrode pair at least at two different positions on the head of a person to be treated, wherein the positions are chosen in such a manner that the trajectories of the applied alternating current signals to be expected cross the target region or cross each other in the target region, and applying an alternating current signal to the plurality of positions for stimulating the deep brain area.

Preferably, the step of successively placing is repeated corresponding to the length of the overall treatment time. Preferably, the alternating current signal is adjusted to a frequency of between 1 kHz and 50 kHz, and/or the alternating current signal is applied as a pulsed alternating current signal, and/or the electrical stimulation parameters such as frequency, amplitude, curve shape and pulse sequence are varied. Preferably, the brain areas to be stimulated are determined before the stimulation treatment, in particular the location and dimensions thereof, again in particular by means of volumetric anatomical image data, e.g CT or MRT.

Additional features and advantages of the invention are shown in the drawings, in which.

Figure 4:
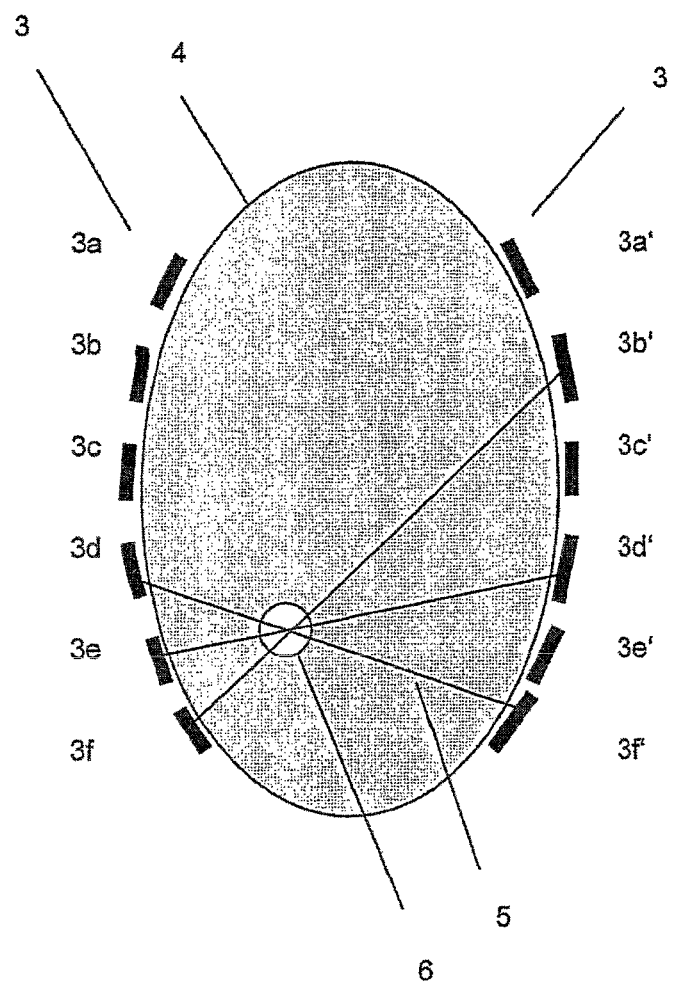
FIG. 4 shows a (top) view of the electrode arrangement operated according to a third modification of the locally focused therapy.
Figure 5:
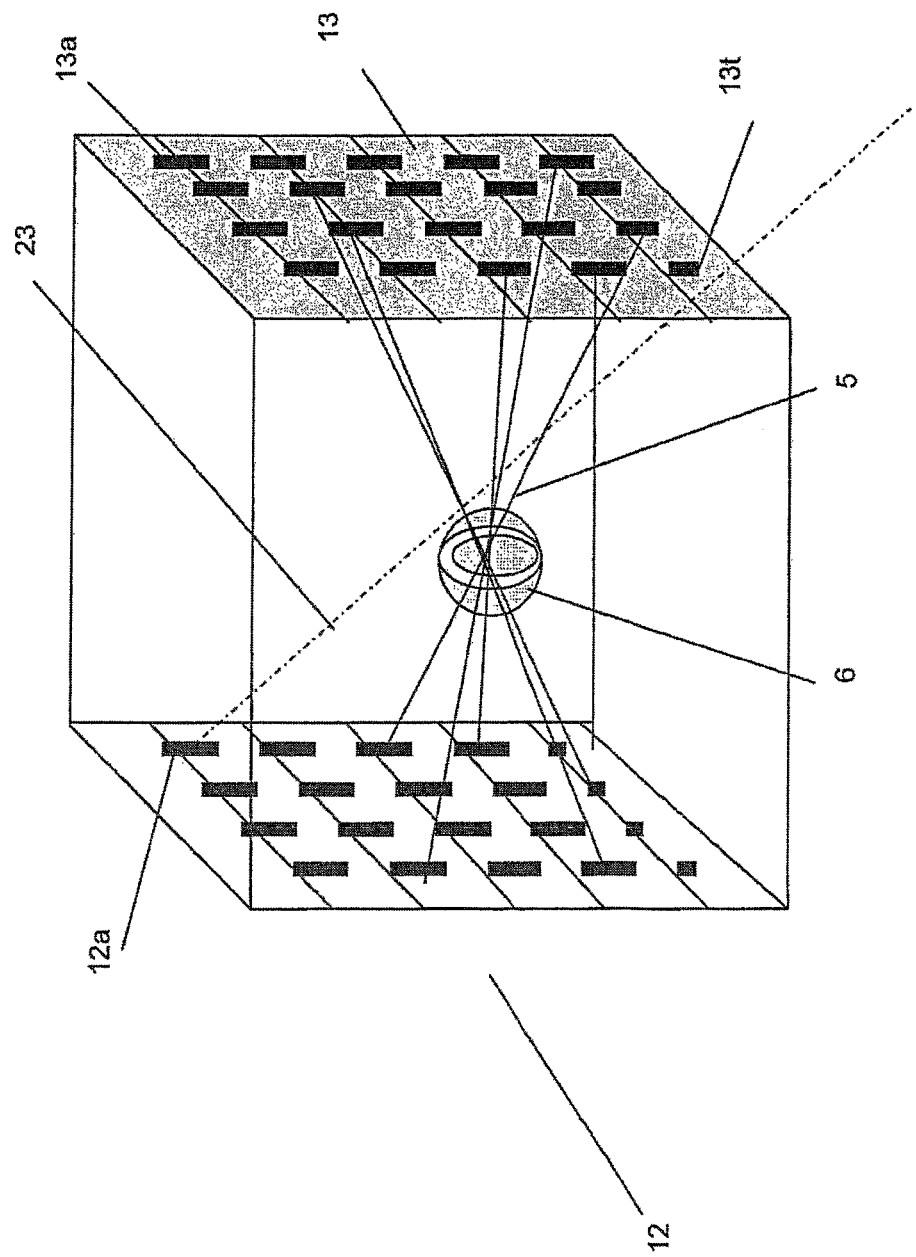
Figure 6:
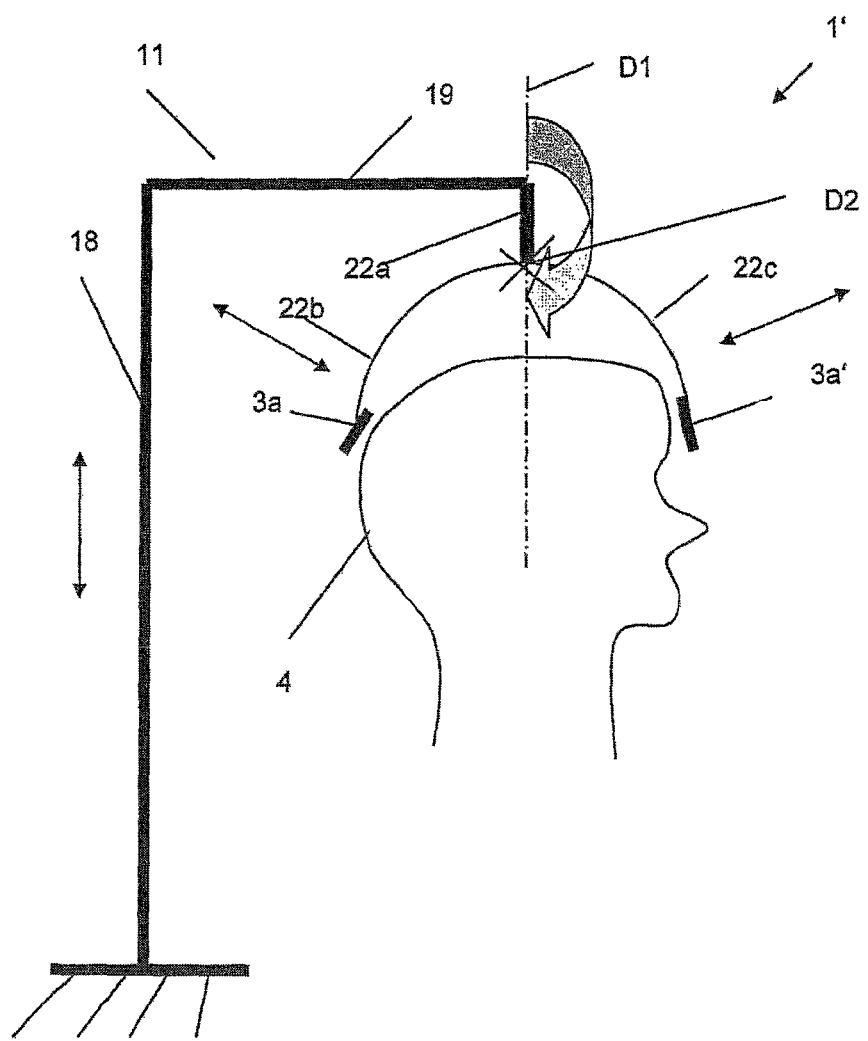

FIG. 5 schematically shows an electrode array pair according to the therapy modification shown in FIG. 4 in a spatial arrangement; and FIG. 6 shows a schematic diagram of a deep brain stimulator comprising a positioning apparatus according to a second preferred embodiment.

Figure 1:
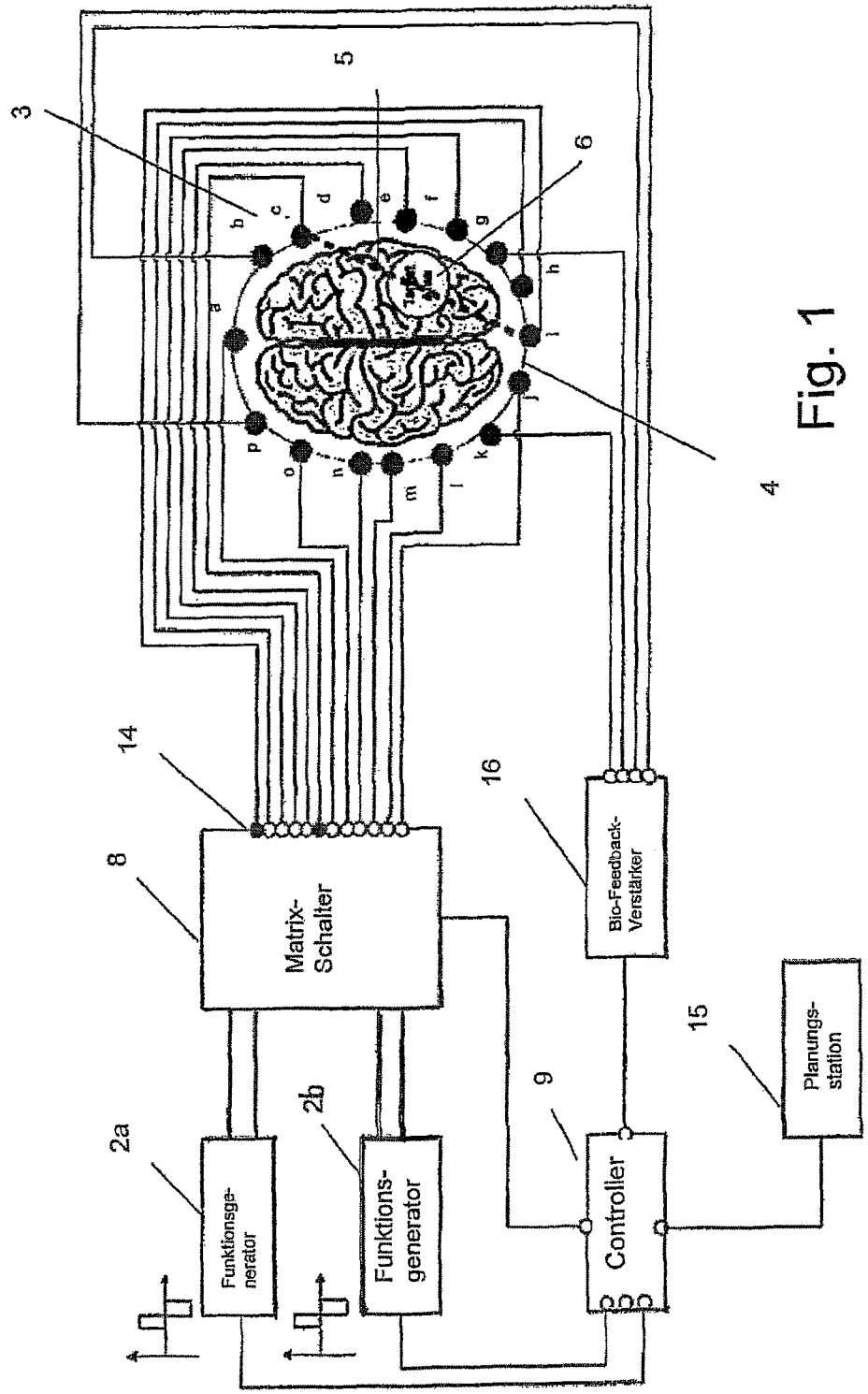
FIG. 1 shows a schematic block diagram of a deep brain stimulator according to a first preferred embodiment.

FIG. 1 shows a first preferred embodiment of an apparatus for the transcranial alternating current stimulation (tASC) of deep brain areas, which will be referred to as deep brain stimulator below and is designated with reference number 1. The deep brain stimulator 1 comprises one or more independent signal generators 2*a*, 2*b* for the generation, for instance, of pulsed electric alternating currents.

The signal generators used are one or more commercially available function generators whose stimulation signals can be freely modulated with respect to frequency, amplitude, curve shape and pulse sequences.

The deep brain stimulator 1 further comprises an electrode arrangement 3 comprising a plurality of electrodes 3*a*-3*p* which are arranged in a manner distributed over the outer circumferential surface of the head 4 of a person to be treated. As is seen in the top view of the head 4, electrodes are positioned on all areas of the head 4, i.e. on the front side, rear side and in the lateral areas.

A matrix switch 8 is arranged between the electrode arrangement 3 and function generators 2*a*, 2*b* and includes a matrix circuit with a total of twelve output terminals 14 which are each assigned and electrically connected to an electrode 3*a*-3*p*. Each output terminal 14 may act as a negative terminal or a positive terminal. The matrix switch 8 assigns signals from a function generator to each selected electrode pair, establishes an electrical connection and interrupts it again. In FIG. 1, the matrix switch 8 selects exactly those pairs of electrodes 3*a*-3*p* whose trajectory 5 crosses the brain area or target region 6 to be treated, that is in FIG. 1, for instance, pair 3*c*-3*i*, and establishes a connection to the function generator 2*a* so that the selected electrode pair 3*c*-3*i* is supplied with a pulsed alternating voltage so as to cause a current flow through the target region 6, and effect a corresponding stimulation in this region.

The choice of the electrode pairs, the assignment between the electrode pairs and the function generators 2*a*, 2*b*, ... and the control of the matrix switch 8 is performed by a controller 9. Controller implies a control unit which controls or regulates the various processes. The controller in the present case is a microcontroller.

The controller 9 is, moreover, electrically connected to the function generators 2*a*, 2*b*. The switching of the electrode pairs 3*a*-3*p* by means of the matrix switch 8 may be coordinated by the controller 9 with the signals of one or more function generators 2*a*, 2*b*. Depending on the therapeutic approach, for instance, different alternating current signals which are provided by different function generators may be applied alternately, or only one alternating current signal of a function generator may be applied via several selected electrode pairs at the same time.

As can be seen in FIG. 1, a planning station 15 is connected to the controller 9, which determines the location and the dimensions of the target region 6 as well as the stimulation parameters, such as signal shape and signal frequency. The planning station 15 has a function to select the electrodes in correspondence with the target region 6. The basis for the target planning are, for instance, volumetric anatomical image data, such as CT or MRT. In addition, the areas may also be delimited by means of functional brain atlases (e.g. atlas by Schaltenbrand-Wahren). Other planning possibilities are based on the use of spatial functional data, such as fMRT, 3D EEG$^2$, or the impedance tomography as will be described in more detail below. Also, it is possible to correlate several data sets with each other (e.g. by the multimodal image data fusion).

The Electrical Impedance Tomography (EIT) is a non-invasive imaging technique by means of which a tomographic image of the brain is obtained on the basis of the conductivity distribution in the brain. Advantageously, the electrode pairs 3$a$-3$p$ placed on the head 4 may be used as sensor elements, wherein a measuring current is supplied at one electrode pair, e.g. 3$a$/3$i$, and an electrical potential distribution can be determined at the other electrode pairs 3$b$-3$h$ & 3$j$-3$p$. The EIT uses the conductivity distribution in a body, which is also dependent, inter alia, on physiological parameters. Thus, the impedance tomography makes it possible to obtain knowledge about the morphology and the function. The measuring currents used are higher-frequency alternating currents in the frequency range of 10 to 100 kHz and have a low current strength in the range of 1 to 10 milliampere, so that no stimulation takes place in the phase of measurement.

According to an inventive approach it is possible to use the process of the impedance tomography as a feedback analysis of the inventive stimulation. This means that the alternating current stimulation is triggered, and the resistance is determined at the same time. The stimulation excites the nerve cells, causing the resistance to become smaller. The stimulation intensity and/or the frequency can then be adapted correspondingly.

In addition, the deep brain stimulator 1 has the possibility to evaluate the success of the therapy by means of bio-feedback and, if applicable, detect dangers to the patient (e.g. epileptic fit). To this end, a feedback data feedback branch is provided, in which a bio-feedback amplifier 16 is interposed between the placed sensor electrodes and the controller 9. Thus, a feedback control system is created to optimize the stimulation parameters, which system is monitored by the controller 9 specifying the respective therapy program.

Below, the operation and mode of operation of the deep brain stimulator 1 will be explained in more detail against the backdrop of a diagnosed disorder.

Initially, the electrodes are placed on the head of the person to be treated. To this end, a plurality of electrodes are advantageously used, which are integrated either in a belt or a cap (not shown in the figure). The electrode belt or electrode cap can be fixed to the head without having regard to the exact target region. Corresponding to the disease pattern certain information relevant for the deep brain stimulation are inputted into the planning station, such as the choice of a special stimulation program and/or the exact coordinates of the target region to be treated. Subsequently, the electrodes are registered with respect to the target region, i.e. the relative location of the target region, on the one hand, and the electrodes, on the other hand, is determined, or a correlation between the electrodes and the target region is determined, respectively. Finally, depending on the therapeutic approach, the number of the alternating current signals used as well as the parameters thereof are inputted, such as the duration of the stimulation, the time sequence of the therapy phases, frequencies of the signals, amplitudes, signal shapes and pulse sequences of the electrical stimulation. Preferably, the controller carries out previously specified therapy programs, so that merely the disease pattern and/or the therapeutic approach have/has to be added in the planning station.

Depending on the inputted coordinates of the target region the controller 9 determines at least one pair of electrodes whose trajectory runs through the area in the brain to be stimulated. As is shown in FIG. 1, the trajectory 5 of the electrode pair designated with reference number 3$c$/3$i$ runs through the target area 6. Depending on the intended therapeutic approach the target area 6 is stimulated correspondingly. Thus, for instance, several pairs of electrodes crossing the target area, for instance also pair 3$f$/3$o$, may be used simultaneously, or sequentially or successively, respectively, namely each with identical or also different signal shapes, amplitudes and frequencies. The different alternating current signals are provided by the plurality of independent function generators 2$a$, 2$b$.

Figure 2:
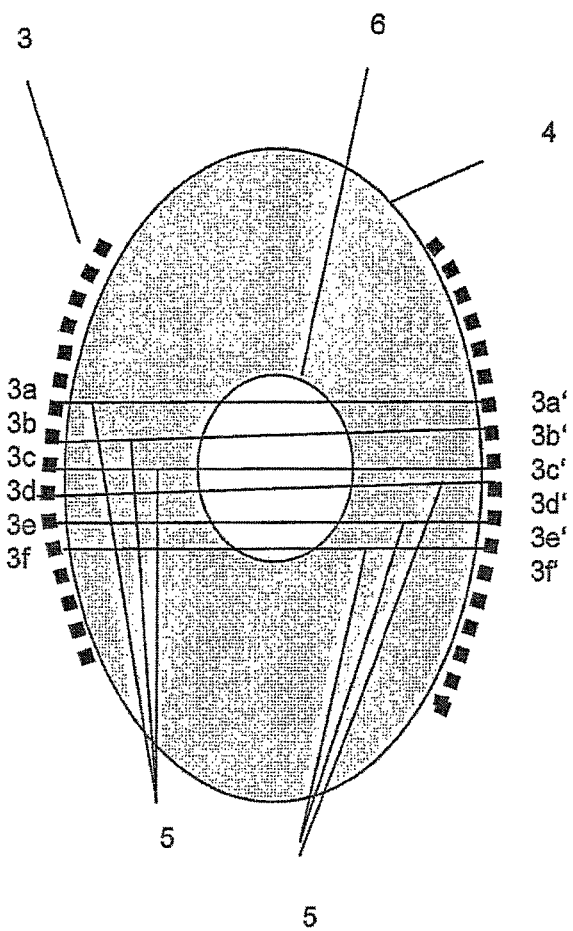
FIG. 2 shows a (top) view of the electrode arrangement operated according to a first modification of the locally focused therapy.
Figure 3:
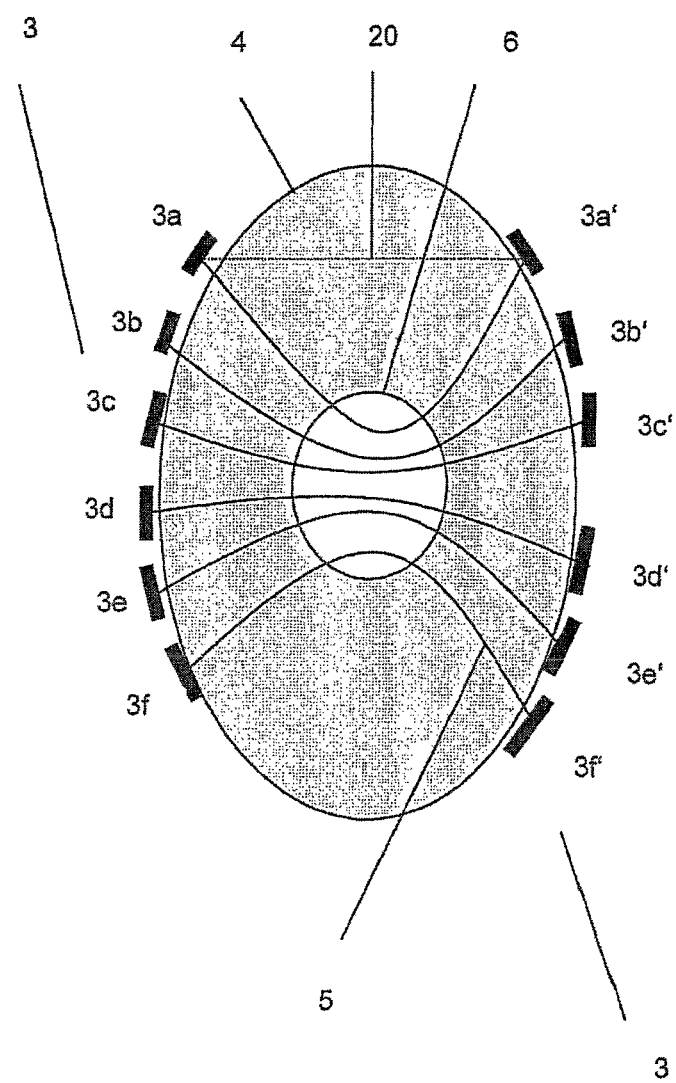
FIG. 3 shows a (top) view of the electrode arrangement operated according to a second modification of the locally focused therapy.

FIGS. 2 to 4 schematically show different modifications for the cortically locally focused therapy, with top views of the head 4 of a person to be treated. According to a first modification the electrode pairs in FIG. 2 are selected such that the trajectories 5 of these electrode pairs, namely the pairs 3$a$/3$a'$, 3$b$/3$b'$, 3$c$/3$c'$, 3$d$/3$d'$, 3$e$/3$e'$ & 3$f$/3$f'$, cross the target area 6 and run substantially parallel to each other. This modification is particularly advantageous if as many closely adjacent electrodes as possible are placed on the head 4 of the person to be treated.

FIG. 3 shows a second modification in which the electrodes are arranged at greater intervals in the circumferential direction around the head 4. In this modification those electrodes 3$a$-3$l$ are chosen as electrode pairs that are arranged on opposite sides of the head 4 and have the smallest distances between each other. Depending on the electrical resistance behavior of the resistance, which results from the transition resistance between the electrode surface and the scalp, and on the resistance properties of the skull and the brain, the current flowing between the respective electrode pairs 3$a$/3$a'$, 3$b$/3$b'$, 3$c$/3$c'$, 3$d$/3$d'$, 3$e$/3$e'$ & 3$f$/3$f'$ is adjusted in such a manner that also the trajectories 5 of electrode pairs whose distance lines would normally not run through the target area, but substantially along a direct distance line 20 (dot-dashed in FIG. 3), adopt arc-shaped and, in particular, parabola-shaped curves, namely in such a manner that the trajectories 5 of these pairs, too, cross the target area 6, as can be seen in FIG. 3.

FIG. 4 shows a third modification in which exactly those pairs of electrodes are selected, namely 3$d$/3$f'$, 3$e$/3$d'$ and 3$f$/3$b'$, whose trajectories 5 cross the target area 6 and whose trajectories 5, again, cross each other in the target area 6. In this modification it is a particular advantage that a greatest possible stimulation can be reached in the target area while, at the same time, the surrounding brain area is stimulated at a minimum. To that effect, the energy supply is focused to the area to be treated, and surrounding area of the brain are affected only to a small extent. Moreover, according to this modification all areas in the brain are accessible despite a smaller number of electrodes.

FIG. 5 schematically illustrates in a three-dimensional view the principle of the cortically locally focused therapy by means of an electrode array pair 12, 13. To simplify the illustration, merely the two electrode arrays 12, 13, each comprising 20 individual electrodes, and the target area 5 of the brain are shown. Each electrode array may also comprise 64 and, preferably, 128 electrodes. As is implied by the continuous lines, exactly four electrode pairs have been selected in this example, whose trajectories 5 cross both the target area 6 and the respective other trajectories in the target area 6. The electrode arrays 12, 13 are arranged in rows and columns in a matrix-like or grid-like manner. However, it is also possible to use other arrangements which are formed differently, for instance, according to the target area to be treated and have areas with a higher and lower electrode density. As is exemplarily illustrated by the dot-dashed line 23 the electrode 12a cannot form a pair with one of the electrodes 13a-13t whose trajectory crosses the target area 6.

FIG. 6 shows a second preferred embodiment of the deep brain simulator according to the invention. The deep brain stimulator 1' comprises a positioning apparatus 11 which is provided in the form of a navigable mechatronic apparatus. On the positioning apparatus 11 an electrode pair 3a, 3a' is arranged. The positioning apparatus 11 comprises a holder which is formed of a height-adjustable support rod 18, in particular a telescopable one, the support rod 18 standing vertically and being mounted on a stationary base. A cantilever arm 19 is fixed to the upper end of the support rod, which preferably projects substantially at a right angle in a horizontal direction. An electrode holder 22 is mounted at the distal end of the cantilever arm 19. The electrode holder 22 comprises a rotatable arm 22a which vertically projects from the distal end of the cantilever arm 19 in a downward direction and is mounted to be rotatable about a vertical axis of rotation D1. The electrode holder 22 further comprises two pivoting arms 22b, 22c which extend radially outwardly from the lower end of the rotatable arm 22a. At the distal ends of the pivoting arms 22b, 22c the electrodes 3a, 3a' are fixed, with the contact surfaces thereof pointing inwardly in the direction of the head to be treated. The pivoting arms 22b, 22c are arc-shaped in a downward direction so as to be capable of placing the electrodes 3a, 3a' in the side region of the skull.

Furthermore, the pivoting arms 22b, 22c are each fixed to the lower end of the rotatable arm 22a to be pivotable about a horizontal axis of rotation D2, so that the pivoting arms 22b, 22c form a gripping arrangement. The gripping movement allows the electrodes 3a, 3a' to be placed against the outside of the head 4 and the movement away from the outside of the head 4. The rotating property of the gripper unit about a vertical axis D1 allows the arrangement of the electrode pair 3a, 3a' on the head 4 in different rotational positions.

In use, the electrodes 3a, 3a' are connected to a (non-illustrated) function generator. Both the function generator and the positioning apparatus 11 are connected to a (non-illustrated) current application control device which controls the positioning process by the positioning apparatus as well as the current application at the electrodes 3a, 3a'. This allows the successive movement to rotational positions in which the electrode pair 3a, 3a, after having been pivoted towards the scalp for placing it on the scalp, can be supplied with a short-term, pulsed alternating current, for the trajectory of which to cross the target area. Preferably, those rotational positions are being traveled to successively in which the trajectories of the applied alternating currents cross each other in the target area.

Preferably, the pivoting arms 22b, 22c are telescopable ones, so that the length thereof is variably adjustable depending on the location of the target area 6 in the head 4. The components known from FIG. 1, e.g. controller, planning station and bio-feedback device, are also transferable to the deep brain stimulator shown in FIG. 6.

The invention claimed is:

1. Apparatus (1) for a transcranial alternating current stimulation (tASC) of deep brain areas, comprising:
    at least one signal generator (2a, 2b) for generating an electrical alternating current signal,
    an electrode arrangement (3) which is adapted to be placed on the head (4) of a person to be treated and which is adapted to be connected electrically to the signal generator (2a, 2b) so as to apply an alternating current signal,
    wherein at least two alternating current signals are applied by means of the electrode arrangement (3), the at least two alternating current signals having trajectories (5) which cross a brain area (6) to be treated,
    wherein the trajectories (5) cross each other in the brain area (6),
    wherein each of the at least two alternating current signals has a frequency of between 1 kHz and 50 kHz, and
    wherein the at least two alternating current signals are applied alternately to the brain area (6).

2. Apparatus according to claim 1,
characterized in that
the alternating current signal is a pulsed alternating current signal.

3. Apparatus according to claim 1,
characterized in that
the electrical stimulation parameters such as frequency, amplitude, curve shape and pulse sequence of the current signal are variable.

4. Apparatus according to claim 1,
characterized in that
the electrode arrangement (3) comprises at least one electrode pair (3a-p, 3a-p; 3a-f, 3a'-f'; 12a-t, 13a-t) including a target electrode (A) and a reference electrode (K), wherein at least one electrode pair (3a-p, 3a-p; 3a-f, 3a'-f'; 12a-t, 13a-t) can be spatially positioned in such a manner that the trajectories (5) of at least two applied current signals cross each other in the brain area (6) to be treated.

5. Apparatus according to claim 1,
characterized in that
a current application control device (7, 7') is provided to control the current signals applied to the at least one electrode pair (3a-p, 3a-p; 3a-f, 3a'-f'; 12a-t, 13a-t).

6. Apparatus according to claim 1,
characterized in that
the electrode arrangement (3) comprises an electrode array pair (12; 13), wherein each electrode array (12; 13) comprises a plurality of electrodes (12a-12t; 13a-13t) arranged in a grid-like or matrix-like manner, wherein one electrode array (12) acts as the target electrode (A) and one electrode array (13) acts as the reference electrode (K), and wherein the number of the target electrodes corresponds to the number of the reference electrodes.

7. Apparatus according to claim 6,
characterized in that
the current application control device (7) is selectively operable so as to select those pairs of electrodes from the plurality of electrodes whose current signal trajectories cross each other in the brain area to be treated.

8. Apparatus according to claim 1,
characterized in that
the current application control device (7) comprises a matrix switch (8), and a controller device (9) controlling the matrix switch (8).

9. Apparatus according to claim 1,
characterized in that
a fixing means is provided for fixing the electrode pair or electrode arrays (12; 13) to the head, in particular to the scalp of the person to be treated.

10. Apparatus according to claim 9,
characterized in that
the fixing means is a belt, a headgear or a cap, and the electrode arrays (12; 13) or electrodes (3a, 3b, . . .; 3a', 3b', . . .) are integrated in the fixing means.

11. Apparatus according to claim 6,
characterized in that
the current application control device (7') comprises a positioning apparatus (11) on which an electrode pair (3a, 3a') is provided, wherein the positioning apparatus (11) is operable to position the electrode pair (3a, 3a') on the head of the person to be treated in a first electrode pair position and in a second electrode pair position, wherein the first and the second spatial electrode pair positions are offset relative to each other in such a manner that the trajectories (5) of the current signals applied in the first and in the second electrode pair positions cross each other in the brain area (6) to be treated, and the current application control device (7') comprises a controller device (9) which controls the operation of the positioning apparatus (11) and the operation of the function generator (2a, 2b) so as to coordinate the positioning of the electrode pair (3a, 3a') and the current application in the different electrode pair positions.

12. Apparatus according to claim 1,
characterized in that
further a planning station (15) is provided for determining the location and the dimensions of the areas of the brain to be stimulated, and the determination is accomplished by volumetric anatomical image data, such as CT or MRT.

13. Apparatus according to claim 1,
characterized in that
a feedback device (16) is provided to supply feedback data concerning the success of the therapy and the medical condition of the patient to the controller device (9) for the further evaluation and optimization of the stimulation parameters.

14. Apparatus according to claim 1,
characterized in that the electrodes (3a..., 3a'...) are planar and preferably have a surface of some $mm^2$ to $cm^2$.

15. Apparatus according to claim 1 for use in a method for treating functional disorders of the brain.

16. Method for a transcranial, non-invasive alternating current stimulation (tACS) of deep brain areas by means of an apparatus according to claim 1, wherein the electrode arrangement (3) of the apparatus includes at least one of 1) at least two electrode pairs (3a, 3a') and 2) an electrode array pair (12; 13), comprising the steps of:
placing the at least two electrode pairs (3a, 3a') at positions on the head of a person to be treated at which the trajectories (5) of the applied alternating current signals cross the brain area (6) to be treated, wherein the trajectories (5) cross each other in the brain area (6); or placing the array pair (12; 13) in correlation with the target region to be treated on the head of a person to be treated and determining the pairs of electrodes (12a-12t; 13a-13t), wherein the trajectories (5) cross the brain area (6) to be treated, and wherein the trajectories (5) cross each other in the brain area (6),
connecting the at least one of the at least two electrode pairs (3a, 3a') and the electrode array pair (12;13) to the at least one signal generator (2a, 2b); and
applying the alternating current signal generated by the at least one signal generator (2a, 2b) to the electrodes for stimulating the brain area (6) to be treated.

17. Method for a transcranial, non-invasive alternating current stimulation (tACS) of deep brain areas by means of the apparatus according to claim 1, wherein the electrode arrangement (3) of the apparatus includes at least one pair of electrodes (3a, 3a''), comprising the steps of:
providing the at least one pair of electrodes (3a, 3a') and connecting the at least one pair of electrodes (3a, 3a') to the at least one signal generator (2a, 2b);
successively placing the at least one electrode pair (3a, 3a') at least at two different positions on the head of a person to be treated, wherein the positions are chosen in such a manner that the trajectories (5) of the applied alternating current signals generated by the at least one signal generator (2a, 2b) to be expected cross the brain area (6) to be treated, and wherein the trajectories (5) cross each other in the brain area (6), and
applying the alternating current signals at the at least two different positions for stimulating the deep brain area (6).

18. Method according to claim 17,
characterized in that
the step of successively placing is repeated corresponding to the length of the overall treatment time.

19. Method according to claim 16,
characterized in that
each of the at least two alternating current signals is applied as a pulsed alternating current signal, and/or the electrical stimulation parameters such as frequency, amplitude, curve shape and pulse sequence are varied.

20. Method according to claim 16,
characterized in that
the brain areas to be stimulated are determined before the stimulation treatment, in particular the location and dimensions thereof, in particular by means of volumetric anatomical image data, e.g CT or MRT.

* * * * *